June 25, 1963 L. F. CAYEUX Plant Pat. 2,265
HYDRANGEA PLANT
Filed Sept. 15, 1961
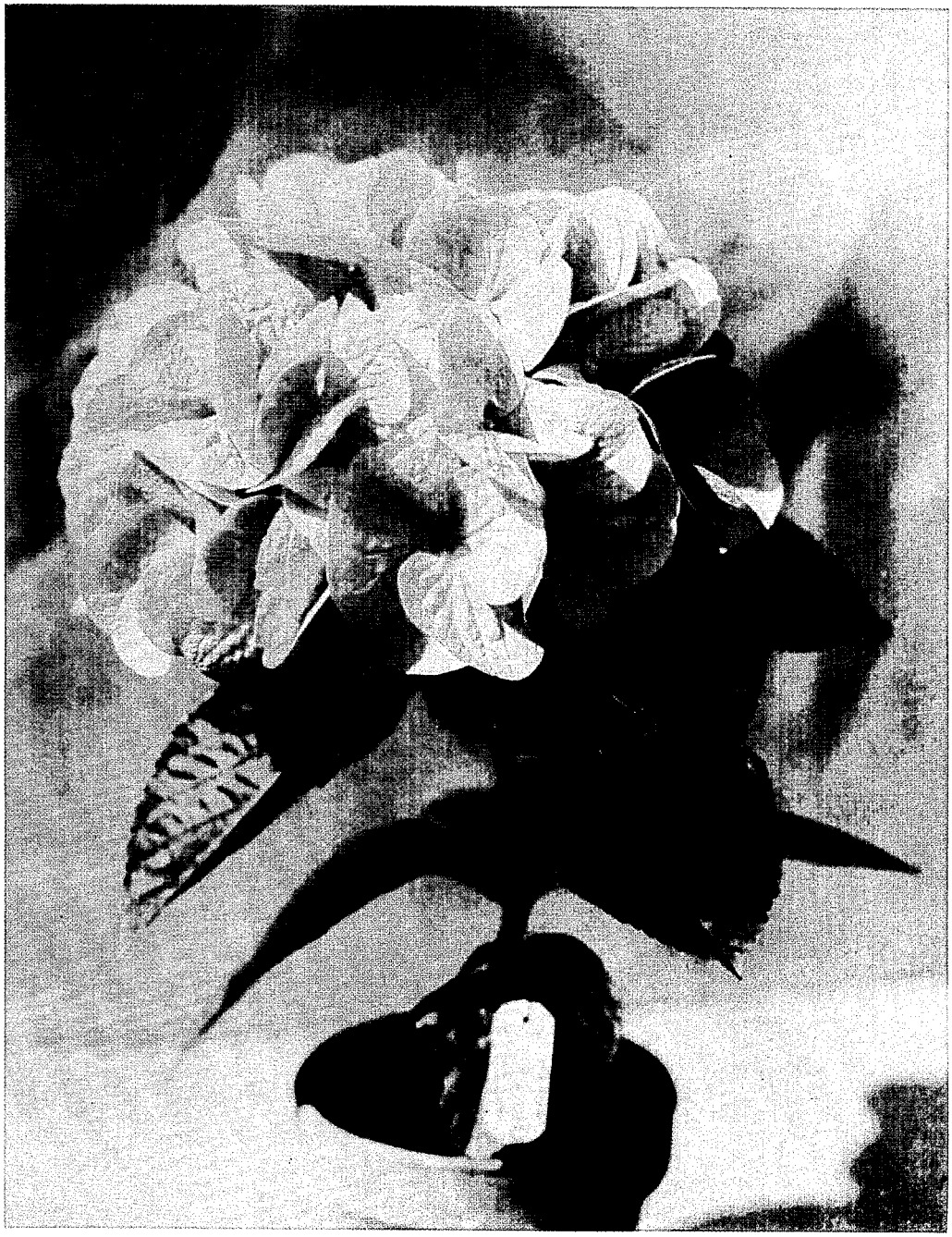
Inventor.
Louis Fernand Cayeux
By: Robb & Robb
Attorneys.

United States Patent Office

Plant Pat. 2,265
Patented June 25, 1963

2,265
HYDRANGEA PLANT

Louis Fernand Cayeux, Le Havre, France, assignor to Roger Talbot, Saint-Symphorien, Indre-et-Loire, France Filed Sept. 15, 1961, Ser. No. 138,536
Claims priority, application France Sept. 24, 1960
1 Claim. (Cl. Plt.—54)

The present invention relates to a new and distinct variety of hydrangea plant which was originated by me as a selected seedling derived by crossing two unnamed and unpatented hydrangea varieties respectively identified in my breeding records as hydrangea varieties No. 133 and No. 24, the former being the seed parent and the latter being the pollen parent.

The primary objective of this breeding was to produce a new hydrangea variety having "embossed" flower petals and a soft or light pink flower color. This objective was fully achieved, along with other desirable features, as evidenced by the following unique combination of characteristics which are outstanding in the new variety and which distinguish it from its parents, as well as from all other hydrangea varieties of which I am aware:

(1) Stocky and medium tall habits of plant growth;
(2) Thick, bright green foliage;
(3) A somewhat elongated leaf shape, with the leaves being serrated around approximately ⅔ of their upper edges;
(4) An early blooming habit;
(5) Flowerheads composed of florets formed of petaloid sepals (pseudo-sepals) of round shape and having small bulges of irregular shape and uneven distribution over their upper surfaces, giving the impression of a distinctive embossed effect thereto;
(6) A distinctive and attractive satiny light pink general color tonality of the flowers, and the ability to readily take on a blue color as the result of adding aluminum sulphate to the soil and/or to the spray water applied to the plants during their culture;
(7) Good disease and weather resistance;
(8) The ability to root easily from slips;
(9) Good forming and keeping qualities of the flower buds; and
(10) Good indoor lasting qualities of the fully open flowers.

Asexual reproduction of the new variety by slip rooting, as performed by me in France, shows that the foregoing characteristics and distinctions come true to form and are established and transmitted through succeeding propagations.

The accompanying drawing shows a typical specimen of the blooming plant of my new hydrangea variety, with the flowers and foliage depicted in color as nearly true as it is reasonably possible to make the same in a color illustration of this character.

The following is a detailed description of the new variety, with color terminolgy in accordance with Seguy's Universal Colour Code, published by Paul Lechevalier, of Paris, France, except where general color terms of ordinary dictionary significance are obvious:

Classification: Hybrid hydrangea (hortensia).

*Plant*

Growth: After nipping off to obtain plants with several flowers, clusters of from 2 to 10 branches fork from the base of the plant and attain a height of from 10 to 12 cm. in summer growth; the nodes occur thereon from 2 to 4 cm. apart; each branch bears from 5 to 8 pairs of leaves; buds form readily and evenly in autumn, and winter conservation is quite good; very good rooting qualities; plant starts to grow early and lends itself quite well to forcing.

Flower stems: Rigid; stout; thick; do not break easily.

*Color.*—Light green, with irregular spots in the form of oval rings of deep red color, No. 113, with a center of the same green color as the stem; spots are very irregularly spaced from about 3 to 7 or 8 cm., and are missing on some portions of the stem.

*Nodes.*—Do not form a circular protuberance around the stem, but appear as bosses at the base of the axial bud and at the attachment point of the leaf petiole; on the flower stems, the distance between the 1st and 3rd nodes ranges from about 4 cm. to 8 cm. while between the 3rd and 4th nodes, the spacing ranges from about 3 to 5 cm., and between the 4th and 6th nodes, the spacing ranges from about 5 to 7 cm.

Leaves: Opposite, with petioles and serrations and a secondary bud at the base of the petiole.

*Petiole.*—Extends up to the tip of the leaf by the axial rib; secondary ribs begin only occasionally from the same point of the axial rib.

*Serrations.*—Serrated only above the lower 3rd of the margin; serrations are short, somewhat spaced towards the base of the leaf, but being more dense towards the upper portion of the leaf.

*Shape.*—General shape is ovoid, but lower portion of its limb remains perpendicular to the petiole for a distance of a few centimeters. Complete; pointed.

*Color.*—Upper side—deep green, No. 416; leaves range lighter in color when plant is in bloom, the farther the leaves are from the flowers, with the green color being as light as No. 372. Lower side—light green, No. 374; green color ranges as light as No. 358 when the plant is in bloom and the farther the leaves are from the flowers.

*Length.*—From about 10.5 to 14 cm.

*Width.*—From about 7.5 to 11 cm.

*Flowers*

Flowerheads (umbel): Composite; terminal; hemispheric; composed of from 50 to 80 florets and sometimes even more. Peduncle—rigid; from about 2 to 4 cm. long.

Barren flowers: Very numerous.

*Peduncle.*—Hollow; about 1.5 mm. in diameter. Color—pink.

*Petals.*—4 petaloid sepals, with free ends being slightly notched, but lateral edges not serrated; width ranges from about 2 to 2.7 cm.; on upper surfaces of petaloid sepals, there are from 5 to 10 bulges forming embossed areas, with the smaller areas being round and the larger ones elongated and having a length of from 2 to 4 mm. and sometimes more. Color—not uniform and lower surfaces being lighter than upper surfaces, while ribs are of darker color; upper side—pink, No. 49; lower side—pink, No. 50, with pink, No. 49.

*Ribs.*—Arranged fan-like with median rib being the most developed, and the secondary ribs extending from the latter and from the radiating ribs, numbering from 4 to 6. Color—pink, No. 48, on upper side and pink, No. 49, on the lower side.

*Elongated petals.*—Flowers include 4 small elongated petals about 1 mm. wide and ranging from about 2.5 to 3 mm. long, and having their edges tucked in toward the central portion of the flower; color of inner surface being pink, No. 53.

*Stamens.*—Number from about 8 to 10; have pink streaks.

Fertile flowers: Scarce; gamosepalous calyx, with usually 5, but sometimes 6 or 7 green serrations; 5 pink petals from 10 to 20 stamens which are pink streaked; one low-positioned ovary; 3 or 4 styles ending in purplish stigmas.

*Endurance*

Disease, pest and cold resistance: Very good resistance to ordinary disease to which hydrangea plants are normally subject, but slightly sensitive to oidium when the weather is raw in summer or autumn; withstands the "anguillule"; and normal winter frosts, all as determined by comparison with other hydrangea varieties grown under the same cultural conditions in France.

I claim:

A new and distinct variety of hydrangea plant, substantially as herein shown and described, characterized particularly as to novelty by the unique combination of stocky and medium tall habits of plant growth, thick and bright green foilage, a somewhat elongated leaf shape, with the leaves being serrated along approximately ⅔ of their upper edges, an early blooming habit, distinctive flowerheads composed of florets formed of petaloid sepals of round shape and having small bulges of irregular shape and uneven distribution over their upper surfaces, giving the impression of an embossed effect thereto, a distinctive and attractive satiny light pink general color tonality of the flowers and the ability to readily acquire a blue color, good disease and weather resistance, the ability to root easily from slips, good forming and keeping qualities of the flower buds, and good indoor lasting qualities of the fully open flowers.

No references cited.